(12) United States Patent
Moor et al.

(10) Patent No.: US 11,864,862 B2
(45) Date of Patent: Jan. 9, 2024

(54) POWER DISTRIBUTION IN A MEDICAL IMAGING SYSTEM

(71) Applicant: Siemens Medical Solutions USA, Inc., Malvern, PA (US)

(72) Inventors: Andrew Philip Moor, Knoxville, TN (US); Nan Zhang, Knoxville, TN (US); Martin Judenhofer, Knoxville, TN (US); Ziad Burbar, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 723 days.

(21) Appl. No.: 16/948,295

(22) Filed: Sep. 11, 2020

(65) Prior Publication Data
US 2022/0079441 A1 Mar. 17, 2022

(51) Int. Cl.
*A61B 5/00* (2006.01)
*H03L 7/14* (2006.01)
*A61B 5/055* (2006.01)

(52) U.S. Cl.
CPC ........... *A61B 5/0033* (2013.01); *A61B 5/055* (2013.01); *H03L 7/145* (2013.01); *A61B 2560/0204* (2013.01)

(58) Field of Classification Search
CPC ..... G05F 1/00; G05F 1/10; G05F 1/12; G05F 1/46; G05F 1/455; G05F 1/45; G05F 1/445; G05F 1/66; G05F 1/40; G05F 1/42; G05F 1/44; G05F 1/462; G05F 1/52; G05F 1/56; G05F 3/10; G05F 3/16; G05F 3/18; G05F 3/185; G05F 3/20; G05F 3/26; G05F 3/30; G05F 3/205; G05F 3/22; G05F 3/24; G05F 3/222; G05F 3/242; G05F 3/225; G05F 3/227; G05F 3/245; G05F 3/247; G05F 3/262; G05F 3/265; G05F 3/267; G05F 1/575; H02M 5/2573; H02M 1/081; H02M 5/293; H02M 7/12; H02M 3/10; H02M 3/125; H02M 3/13; H02M 3/135; H02M 3/145; H02M 3/15; H02M 3/155; H02M 3/156; H02M 3/157; H02M 3/158; H02M 1/346; H02M 3/1588; H02M 2003/1566; H02M 3/1582; H02M 3/1584; H02M 2003/1557; H02M 1/0032; H02M 1/4225; H02M 7/217; H02M 1/0025; H02M 1/0045; H05B 39/048; B23K 11/24; H04B 2215/069
See application file for complete search history.

(56) References Cited

U.S. PATENT DOCUMENTS

| 9,634,567 B2 * | 4/2017 | Oliaei .................... G01D 11/00 |
| 9,823,320 B2 * | 11/2017 | Model .................... G01R 33/36 |
| 10,274,990 B1 * | 4/2019 | Chang ..................... H03K 5/24 |

(Continued)

*Primary Examiner* — Jeffrey A Gblende

(57) ABSTRACT

A framework for power management. The framework includes at least one power distribution board disposed within a radio-frequency (RF) cabin of a medical imaging system and coupled to an external reference clock. The power distribution board may include a clock circuit that generates one or more output clock signals based on a reference clock signal from the external reference clock. One or more switching regulators may be coupled to the clock circuit. The one or more switching regulators may be synchronized to the one or more output clock signals and provide power to one or more endpoint loads.

20 Claims, 3 Drawing Sheets

(56) References Cited

U.S. PATENT DOCUMENTS

| | | | |
|---|---|---|---|
| 10,622,979 B2* | 4/2020 | Jiang | H03K 5/1252 |
| 11,095,206 B2* | 8/2021 | Oh | H02M 1/083 |
| 11,554,261 B2* | 1/2023 | Baandrup | A61N 1/36062 |
| 2009/0018442 A1* | 1/2009 | Miller | G01S 15/8906 |
| | | | 600/437 |
| 2014/0121453 A1* | 5/2014 | Maslowski | A61B 5/0046 |
| | | | 600/27 |
| 2018/0280001 A1* | 10/2018 | Iwama | H02J 7/00 |

* cited by examiner

POWER DISTRIBUTION IN A MEDICAL IMAGING SYSTEM

TECHNICAL FIELD

The present disclosure generally relates to power distribution, and more particularly to power distribution in a medical imaging system.

BACKGROUND

In a digital or analog system, a regulated power supply is often necessary. There are generally two methods to convert an input voltage to the desired output voltage. The first method uses a linear regulator, which converts a higher input voltage to a lower desired output voltage by dissipating the excess energy from the input voltage as waste heat. Linear regulators are easy to use and inexpensive, but they are typically inefficient. They generate a lot of waste heat which must be dissipated with bulky and expensive heatsinks. The larger the difference between the input and output voltages, the more heat is produced.

The second method uses a switching regulator (or DC(direct current)-DC converter) for non-linear conversion. The switching regulator converts an input voltage to an output voltage by temporarily storing the input voltage energy and later releasing the energy at a different output voltage. This is accomplished with the help of an electrical switch and a controller which regulates the rate at which energy is transferred to the output. The efficiency of switching regulators is much higher, and they can power useful load from higher voltage sources since their efficiency is less dependent on input voltage.

In the context of magnetic resonance (MR) imaging-positron emission tomography (PET) hybrid medical imaging systems, the use of switching regulators has traditionally been restricted to placing them outside of the radiofrequency (RF) cabin that encloses the MR system and suppresses RF signals. By placing the switching regulator outside the RF cabin, the risk of switching noise being coupled into the RF spectrum used for MR imaging is minimized.

SUMMARY

Described herein is a framework for power management. The framework includes at least one power distribution board disposed within a radio-frequency (RF) cabin of a medical imaging system and coupled to an external reference clock. The power distribution board may include a clock circuit that generates one or more output clock signals based on a reference clock signal from the external reference clock. One or more switching regulators may be coupled to the clock circuit. The one or more switching regulators may be synchronized to the one or more output clock signals and provide power to one or more endpoint loads.

BRIEF DESCRIPTION OF THE DRAWINGS

A more complete appreciation of the present disclosure and many of the attendant aspects thereof will be readily obtained by reference to the following detailed description when considered in connection with the accompanying drawings.

DETAILED DESCRIPTION

Figure 1:
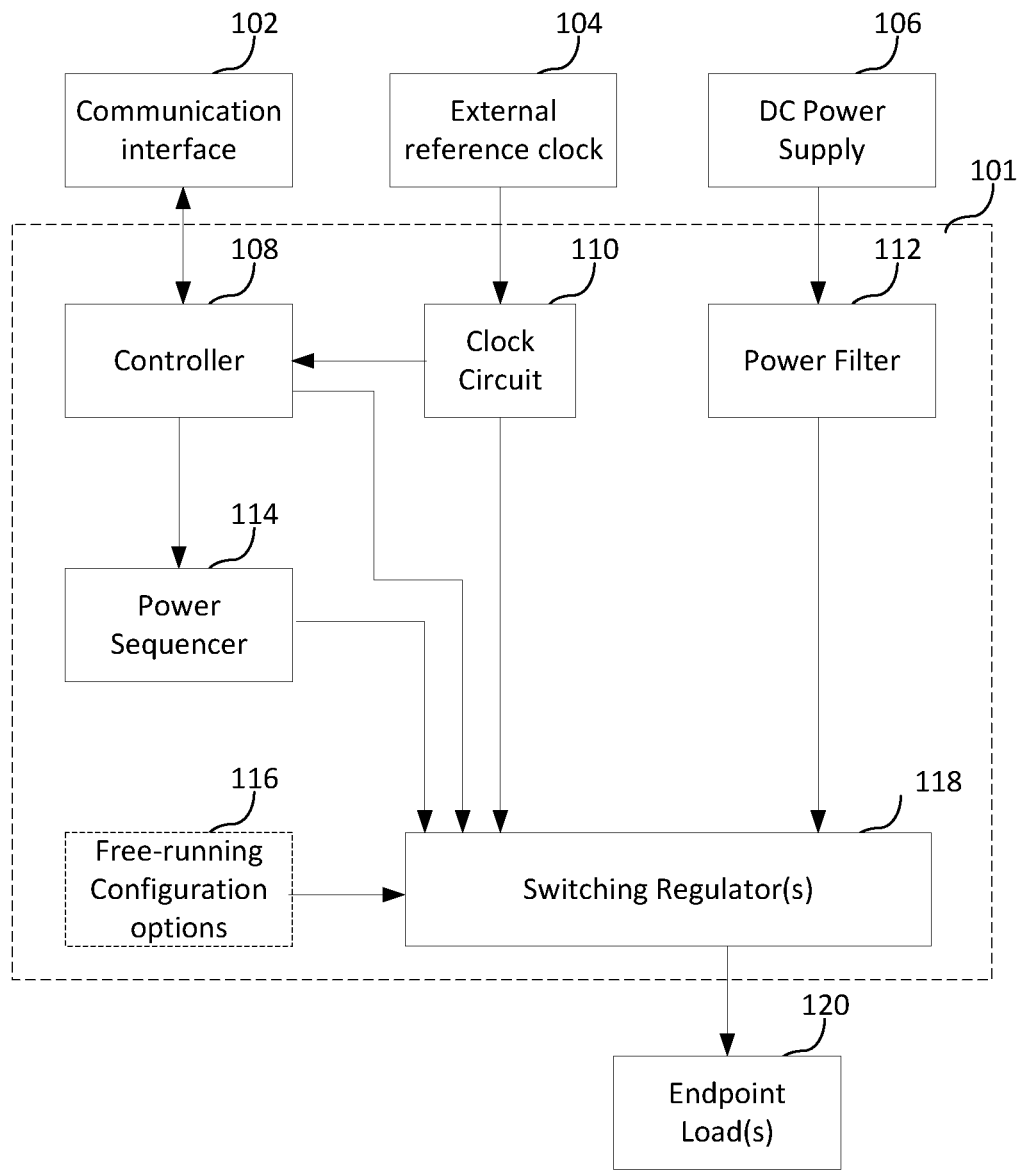
FIG. 1 shows an exemplary power management system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

New technology for switching regulators has enabled substantially higher switching frequencies, which can be designed to operate in a spectral region outside of the range required by medical imaging systems, such as a 3-Tesla MR scanner. Typically, frequencies which sit on an integer multiple of 2.5 MHz are not observed in the MR image acquired by the 3-Tesla MR scanner. The switching regulators may be designed to operate at 2.5 MHz, but care must be taken to ensure that the actual frequency used is derived from the same reference frequency used by the MR scanner—otherwise, small deviations in the absolute frequency can be observed as harmonics inside the MR scanner's spectral region of interest.

A framework for power management is described herein. In accordance with one aspect, the framework allows a single direct current (DC) power supply to be used to generate multiple power rails inside the RF cabin of a medical imaging system. The framework may include a power distribution board that provides an input for a reference clock and an associated clock management device for producing a frequency-locked deterministic-phase set of output clocks that can drive switching regulators. The framework also enables operation of the switching regulators in a self-drive mode, to power the clock management electronics and then transition seamlessly into a "forced" clock mode once the clock management is operational. The output voltage and current of each derived power rail may be monitored, controlled and/or adjusted.

The present framework enables the use of switching regulators inside the RF cabin without disturbing the spectral regions used for the medical imaging (e.g., MR). Switching regulators are desirable because they are more power-efficient, which translates to a lower demand on the electronics cooling system. The present framework solves the problem of guaranteeing frequency synchronization of the switching regulators with the system reference clock, while also providing a means to control and monitor the power provided by each switching regulator.

The present framework also provides the ability to use a single DC voltage to power an entire segment of the PET gantry while minimizing losses due to conversion to lower voltages at the point of load. The present framework thereby solves the problems associated with bringing multiple different DC voltages into the RF cabin from a set of external sources. Using a single supply voltage advantageously reduces the cabling requirements from outside the RF cabin, simplifies assembly and testing, and reduces the complexity of maintaining RF cabin integrity. These and other exemplary features and advantages will be described herein.

FIG. 1 shows an exemplary power management system 100. Power management system 100 includes a communication interface 102, external reference clock 104 and direct current (DC) power supply 106 coupled to a power distribution board 101. Power distribution board 101 provides power to one or more endpoint loads 120. Power distribution board 101 may be disposed inside, for example, a radio-frequency (RF) cabin of a medical imaging system. The RF cabin may be a room or other enclosure configured with one or more RF shields to reduce RF noise within the medical scanning environment.

The medical imaging system is a radiological imaging device that acquires medical image data that reveals internal structures hidden by skin and bones of the subject. Such medical imaging system may use technologies of X-ray radiography, computed tomography (CT), magnetic resonance (MR) imaging, ultrasound, endoscopy, elastography, tactile imaging, thermography, medical photography, nuclear medicine functional imaging techniques (e.g., positron emission tomography (PET), single-photon emission computed tomography (SPECT)), or a combination thereof. In some implementations. the medical imaging system is a hybrid medical imaging device, such as a magnetic resonance (MR) imaging-positron emission tomography (PET) scanner.

Communication interface 102 allows power distribution board 101 to receive commands and provide status information to upper level system components. Upper level system components may include, for instance, a processor, controller, microcontroller and/or non-transitory computer-readable media in a medical imaging system. Communication interface 102 may include, but is not limited to, an Ethernet bus, a universal serial bus (USB) bus, RS-232, Controller Area Network (CAN) bus, or any bus conforming to other industrial standard communication protocol. The physical media used for the communication interface 102 may be electrical or optical.

External reference clock 104 provides a reference clock signal as the master clock to enable synchronization of switching regulators 118 with an external device. The interface may be electrical or optical, and the reference frequency may be selected based on the requirements of the switching regulators 118 to be synchronized. The frequency of the reference clock signal may be deterministically correlated with the operating frequency used by the medical imaging system. For instance, an MR medical scanner may use multiple specific operating frequencies that are derived using integer or fractional relationships from a single reference oscillator. Reference clock 104 may be derived from the same single reference oscillator as the MR medical scanner by using an integer (e.g., 1, 2, 3, etc.) or fractional relationship (e.g., 1.5, 2.5, etc.).

DC power supply 106 may be provided from a bulk supply outside the RF cabin. DC power supply 106 provides a single DC voltage and associated ground return. The DC voltage may be an industry-standard distribution voltage, such as 12V or 24V, but the specific implementation may be tailored to optimize the performance of the switching regulator(s) 118. One DC power supply 106 may be used to drive multiple power distribution boards 101. Alternatively, each board 101 may be provided with a dedicated DC power supply 106.

Power distribution board 101 may include a controller 108, a clock circuit 110, a power filter 112, a power sequencer 114, configuration options 116 and one or more switching regulators 118. Controller 108 is coupled to the communication interface 102 to receive and execute commands and to provide status information to one or more upper level system components. Exemplary commands include, but are not limited to, "turn on/off one of the switching regulators to control downstream endpoint loads", "adjust output voltage of one of the switching regulators", "change switching frequency by adjusting clock circuit settings", etc. Exemplary status information includes, but is not limited to, operation status of switching regulator, temperature of power distribution board or components thereof, load current of endpoint, validity status of clock signal to clock circuit 110, etc. Controller 108 may be a simple controller such as a Programmable Intelligent Computer (PIC), single-board microcontroller (e.g., Arduino), or Advanced RISC (Reduced Instruction Set Computing) Machine (ARM)-based microcontroller. Alternatively, controller 108 may be instantiated as a soft-core microprocessor or state machine inside a field-programmable gate array (FPGA), or with a system-on-chip (SoC) device.

Clock circuit 110 is coupled to the reference clock 104 and provides one or more clean output clock signals to one or more switching regulators 118. Clock circuit 110 may include a simple buffer, a clock divider that provides an output signal that is a fixed, smaller ratio of input signal, a clock synthesizer, or a combination thereof. In some implementations, clock circuit 110 may also incorporate a phase-locked loop (PLL) to allow other frequencies to be derived from the external reference clock 104. More particularly, the clock circuit 110 may provide an output signal that is based on a phase-locked loop (PLL) that is locked to the input reference clock signal, and then divided using an integer or fractional configuration to produce frequency-locked deterministic-phase set of output clock signals which may be at a higher or lower frequency than the input signal. Clock circuit 110 may optionally provide a jitter cleaning function. At least one output of the clock circuit 110 may be reserved to enable daisy-chaining of the reference clock 104 to a downstream power distribution board, if desired.

Power filter 112 is coupled to DC power supply 106 to generate filtered power by removing unwanted noise from the incoming DC power feed, and provides bulk capacitance to minimize load transients on the DC power feed when downstream power demands shift. Power filter 112 also helps prevent switching noise associated with components inside the power distribution board 101 from propagating backwards down the DC power feed line. Power filter 112 is coupled to the switching regulator(s) 118 to provide the filtered power.

Power sequencer 114 is coupled to the controller 108 and switching regulator(s) 118 to ensure that each of the switching regulator(s) 118 follows a pre-defined sequence (including ramp rates, if applicable) for startup and shutdown. Power sequencer 114 may be, for example, a purpose-specific integrated circuit (IC), or it can be integrated into the controller 108 with appropriate input/output (I/O) connections to the switching regulators 118.

Free-running configuration options 116 are coupled to the switching regulator(s) 118 to ensure that the switching regulator(s) 118 are able to operate in a stable and predictable manner to power the endpoint load(s) 120 even when the external reference clock 104 is invalid or unavailable. Configuration options 116 may include bootstrapping resistors or other methods of ensuring that parameters of the switching regulator(s) 118 are placed in a known state. Those parameters include, but are not limited to, free-running switching frequency, default load state (on/off), ramp rate, fault threshold (e.g., short-circuit detection), etc. Such parameters may vary depending on the particular switching regulator(s) 118 used.

Switching regulator(s) 118 are coupled to the power sequencer 114, controller 108, clock circuit 110, power filter 112 and free-running configuration options 116. Switching regulator(s) 118 may be synchronized to the output clock signal from clock circuit 110. In some implementations, switching regulator(s) 118 may operate in "forced" clock mode based on a clock frequency that avoids overlapping with any spectral region of interest in the medical imaging system. For example, if the medical imaging system is a 3-Tesla MR system, the clock frequency may be 2.5 MHz or any integer multiples of 2.5 MHz to avoid overlapping with the medical imaging system's spectral regions of interest.

Switching regulator(s) 118 may operate in a self-drive mode to power the clock circuit 110, and then transition seamlessly into a "forced" clock mode in response to the clock circuit 110 being operational and input clock signal from clock circuit 110 being valid. In some implementations, controller 108 may monitor the status of the clock circuit 110 and provide a signal to the switching regulator(s) 118 to indicate that the clock circuit 110 is operational. Alternatively, the switching regulator(s) 118 may dynamically detect the absence of an input clock signal and "fall back" to a local oscillator-based frequency reference that is either fully or partially built into the regulator(s) 118.

Switching regulator(s) 118 provide high-efficiency conversion of the filtered DC power from the power filter 112 to different power rails at different voltages. The specific voltages generated can be either higher or lower than the DC power supply 106, based on the topology of the switching regulator 118. For instance, a 24-volt DC power supply 106 may be converted to a high voltage appropriate for Silicon photomultiplier (SiPM) bias, as well as 5V, 3.3V, 1.8V and similar lower voltages required by PET readout electronics.

Each switching regulator 118 may incorporate appropriate output power filtering to ensure load transients are well-managed and switching noise is reduced to an acceptable level for the target design. Each switching regulator 118 may monitor the output voltage and current of each derived DC power rail. On/off control and/or output voltage adjustment for one or more of the derived power rails may be provided. In some implementations, controller 108 may query and manage the switching regulator 118 based on the regulator's specific capabilities. Monitoring and control functions may be integrated in the switching regulator 118 and accessed by controller 108 via, for example, an Inter IC ($I^2C$ or IIC) bus or Serial Peripheral Interface (SPI) bus connection.

Switching regulator(s) 118 provide power to one or more endpoint loads 120. Endpoint load(s) 118 are typically other major circuit elements which require multiple DC power rails with specific sequencing requirements. Examples include, but are not limited to, circuit boards using FPGAs, SOCs, MCUs, memory or other processing elements of a medical imaging system.

Figure 2:
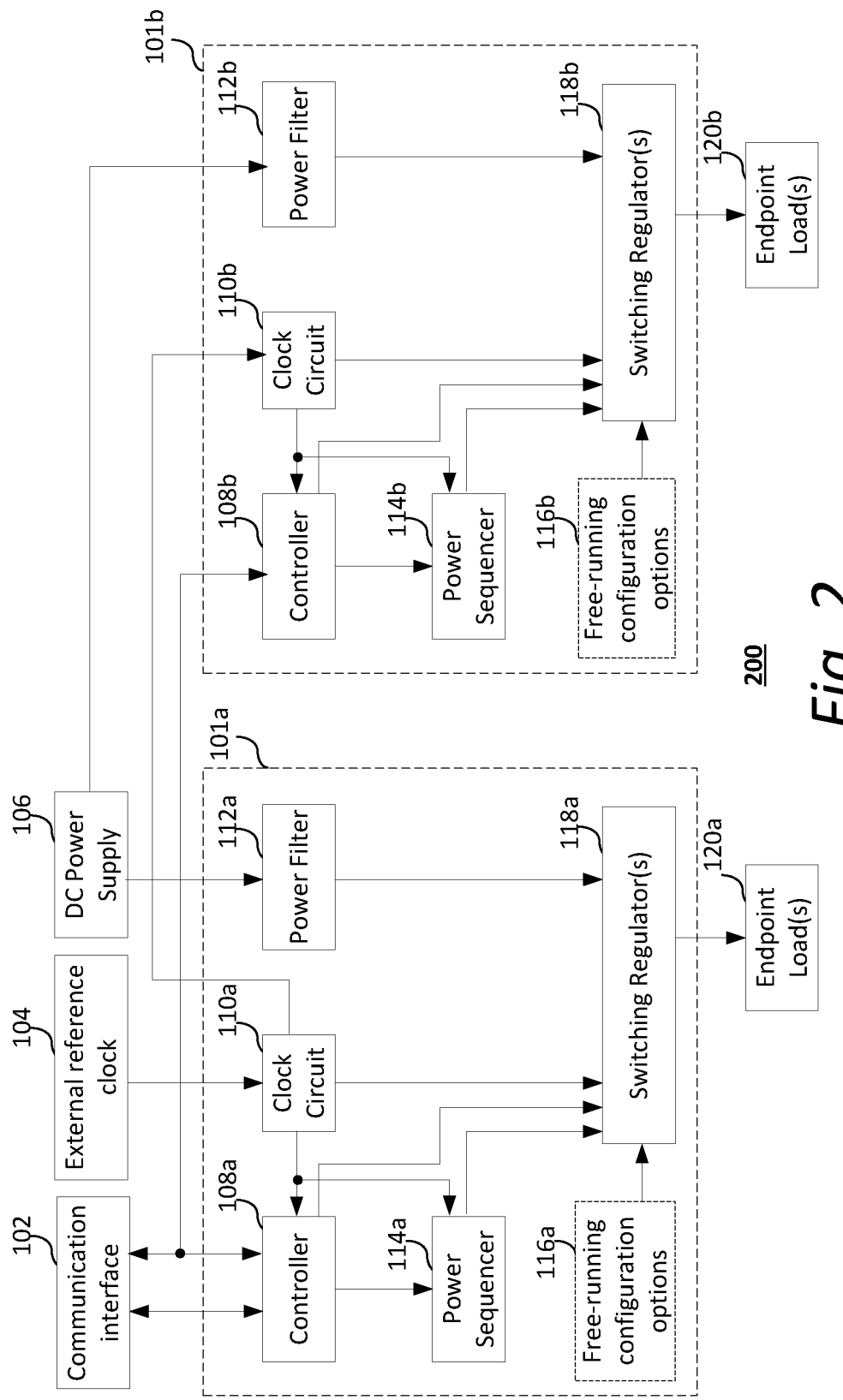
FIG. 2 shows another exemplary power management system.

FIG. 2 shows another exemplary power management system 200. Power management system 200 provides a single system interface (i.e., communication interface 102, external reference clock 104, DC power supply 106) that drives two power distribution boards 101a and 101b with minimal cabling and interconnect overhead. It should be appreciated that more than two power distribution board instances may also be provided. Each power distribution board (101a, 101b) may include similar components, such as a controller (108a, 108b), a clock circuit (110a, 110b), power filter (112a, 112b), power sequencer (114a, 114b), free-running configuration options (116a, 116b), one or switching regulators (118a, 118b), and one or more endpoint loads (120a, 120b).

Each power distribution board (101a, 101b) may support daisy-chaining of the reference clock 104 via the clock circuit (110a, 110b). Any number of output clock signals may be provided by the clock circuit 110a to enable any number of downstream boards to be connected and synchronized in the topology which is most convenient for the design. Each power distribution board (101a, 101b) may also support daisy-chaining of the communication interface 102. This enables a single system interface to communicate with multiple power distribution board instances with minimal cabling and interconnect overhead. The topology of the daisy chain may be a shared multi-drop bus, serial pass-through, Ethernet switching, or other industry-proven architecture. Other topologies, such as star or trunk-branch-leaf topologies, are also possible. The physical media used for daisy-chaining may be electrical or optical.

Figure 3:
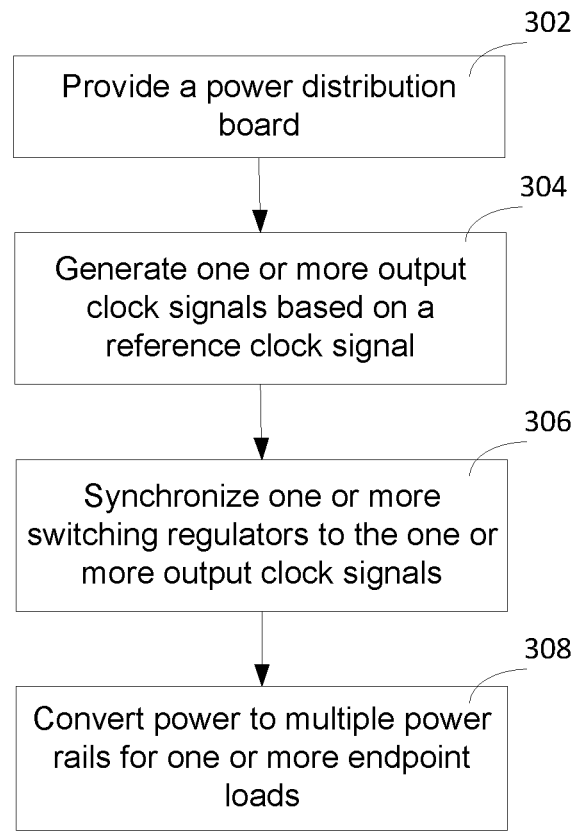
FIG. 3 shows an exemplary method of power management.

FIG. 3 shows an exemplary method 300 of power management. It should be understood that the steps of the method 300 may be performed in the order shown or a different order. Additional, different, or fewer steps may also be provided. Further, the method 300 may be implemented with the system 100 of FIG. 1, system 200 of FIG. 2, a different system, or a combination thereof.

At 302, a power distribution board 101 is provided. The power distribution board 101 may be provided inside a radio-frequency (RF) cabin of a medical imaging system. The power distribution board 101 may provide input lines for a communication interface 102, external reference clock 104 and direct current (DC) power supply 106. The power distribution board 101 may include a controller 108, a clock circuit 110, a power filter 112, a power sequencer 114, configuration options 116 and one or more switching regulators 118.

At 304, clock circuit 110 generates one or more output clock signals based on a reference clock signal from external reference clock 104. Clock circuit 110 may provide an output signal that is based on a phase-locked loop (PLL) that is locked to the input reference clock signal, and then divided using an integer or fractional configuration to produce frequency-locked deterministic-phase set of output clock signals which may be at a higher or lower frequency than the input signal.

At 306, one or more switching regulators 118 are synchronized to the one or more output clock signals. In some implementations, switching regulator(s) 118 may operate in "forced" clock mode with a fixed clock frequency that avoids overlapping with any spectral region of interest in the medical imaging system. For example, if the medical imaging system is a 3-Tesla MR system, the clock frequency may be 2.5 MHz or any integer multiples of 2.5 MHz to avoid overlapping with the medical imaging system's spectral regions of interest. Switching regulator(s) 118 may operate in a self-drive mode to power the clock circuit 110, and then transition seamlessly into a "forced" clock mode in response to the clock circuit 110 being operational and input clock signal from clock circuit 110 being valid.

At 308, switching regulator(s) 118 converts power to multiple power rails for one or more endpoint loads 120. The input power to the switching regulator(s) 118 may be provided by a power filter 112 coupled to the DC power supply 106. Additionally, each switching regulator 118 may incorporate appropriate output power filtering to ensure load transients are well-managed and switching noise is reduced to an acceptable level for the target design. Each switching regulator 118 may monitor the output voltage and current of each derived DC power rail. On/off control and/or output voltage adjustment for one or more of the derived power rails may be provided. In some implementations, controller 108 may query and manage the switching regulator 118 based on the regulator's specific capabilities. Monitoring and control functions may be integrated in the switching regulator 118 and accessed by controller 108.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A power management system, comprising:
   at least one power distribution board disposed within a radio-frequency (RF) cabin of a medical imaging system, wherein the power distribution board is directly coupled to an external reference clock and a single power supply outside the RF cabin, and includes
      a clock circuit that generates one or more output clock signals based on a reference clock signal from the external reference clock, and
      one or more switching regulators coupled to the clock circuit, wherein the one or more switching regulators are synchronized to the one or more output clock signals, wherein the one or more switching regulators provide power from the single power supply to one or more endpoint loads.

2. The power management system of claim 1 wherein the medical imaging system comprises a magnetic resonance (MR) imaging-positron emission tomography (PET) scanner.

3. The power management system of claim 1 wherein the external reference clock is derived from a same reference oscillator used by the medical imaging system to generate at least one operating frequency.

4. The power management system of claim 1 wherein the power distribution board further includes a controller coupled to a communication interface to receive and execute commands and provide status information.

5. The power management system of claim 1 wherein the clock circuit comprises a simple buffer, a clock divider, a clock synthesizer or a combination thereof.

6. The power management system of claim 1 wherein the clock circuit comprises a phase-locked loop.

7. The power management system of claim 6 wherein the phase-locked loop generates one or more frequency-locked deterministic-phase output clock signals that drive the one or more switching regulators.

8. The power management system of claim 1 wherein at least one output of the clock circuit is reserved for daisy-chaining the reference clock signal to a downstream power distribution board.

9. The power management system of claim 1 wherein the power distribution board further includes a power filter that removes noise from incoming power feed from a power supply and generates filtered power for the one or more switching regulators.

10. The power management system of claim 1 wherein the power distribution board further includes a power sequencer coupled to the one or more switching regulators that ensures the one or more switching regulators follow a pre-defined sequence for startup and shutdown.

11. The power management system of claim 1 wherein the power distribution board further includes one or more bootstrapping resistors that place one or more parameters of the one or more switching regulators in a known state.

12. The power management system of claim 4 wherein the controller monitors the clock circuit and provides a signal to the one or more switching regulators to indicate that the clock circuit is operational.

13. The power management system of claim 4 wherein the controller manages the one or more switching regulators.

14. A power management system, comprising:
    first and second power distribution boards disposed within a radio-frequency (RF) cabin of a medical imaging system, wherein the first and second power distribution boards are directly coupled to an external reference clock and a single power supply outside the RF cabin, wherein each of the first and second power distribution boards includes
       a clock circuit that generates one or more output clock signals based on a reference clock signal from the external reference clock, and
       one or more switching regulators coupled to the clock circuit, wherein the one or more switching regulators are synchronized to the one or more output clock signals, wherein the one or more switching regulators provide power from the single power supply to one or more endpoint loads.

15. The power management system of claim 14 wherein the one or more endpoint loads comprise multiple circuit elements that require multiple power rails.

16. The power management system of claim 14 wherein the clock circuit of the first power distribution board provides at least one of the one or more output clock signals to the clock circuit of the second power distribution board.

17. The power management system of claim 14 wherein the first and second power distribution boards are coupled to a single communication interface.

18. A method of power management, comprising:
    providing a power distribution board within a radio-frequency (RF) cabin of a medical imaging system, wherein the power distribution board includes a clock circuit and one or more switching regulators, wherein the power distribution board is directly coupled to a single power supply outside the RF cabin;
    generating, by the clock circuit, one or more output clock signals based on a reference clock signal;
    synchronizing the one or more switching regulators to the one or more output clock signals; and
    converting, by the one or more switching regulators, power from a single power supply outside the RF cabin to multiple power rails inside the RF cabin for one or more endpoint loads.

19. The method of claim 18 wherein generating the one or more output clock signals comprises generating one or more frequency-locked deterministic-phase output clock signals.

20. The method of claim 18 further comprises monitoring the clock circuit and providing a signal to the one or more switching regulators to indicate that the clock circuit is operational.

* * * * *